United States Patent [19]
Chaovapong et al.

[11] Patent Number: 6,103,879
[45] Date of Patent: Aug. 15, 2000

[54] BIVALENT MOLECULES THAT FORM AN ACTIVATING COMPLEX WITH AN ERYTHROPOIETIN RECEPTOR

[75] Inventors: Warak Lee Chaovapong, San Diego; Lutz B. Giebel, San Mateo, both of Calif.; Cyrus Karkaria, Cambridge, Mass.; Michael J. Ross, San Mateo, Calif.; Helmut H. Schneider, San Francisco, Calif.; Kevin Shoemaker, San Francisco, Calif.

[73] Assignee: Axys Pharmaceuticals, Inc., South San Francisco, Calif.

[21] Appl. No.: 08/876,813

[22] Filed: Jun. 16, 1997

Related U.S. Application Data

[60] Provisional application No. 60/059,063, Jun. 21, 1996.
[51] Int. Cl.[7] .......................... C07K 16/18; C07K 16/28; C12N 5/12
[52] U.S. Cl. ..................................... 530/388.1; 530/388.2; 530/387.1; 435/326; 435/332; 424/141.1; 424/152.1
[58] Field of Search ............................. 530/387.1, 388.1, 530/388.15, 388.2, 388.22, 389.1, 391.3; 435/334, 130.1, 141.1, 142.1, 143.1, 152.1

[56] References Cited

FOREIGN PATENT DOCUMENTS

| | | |
|---|---|---|
| WO 90/08822 | 8/1990 | WIPO . |
| WO 92/21029 | 11/1992 | WIPO . |
| WO 96/03438 | 2/1996 | WIPO . |
| WO 96/40231 | 12/1996 | WIPO . |

OTHER PUBLICATIONS

Waldmann, Science 252:1657, 1991.
S. Elliott Et Al.: "Isolation and Characterization of RhuEPO Receptor Monoclonal Antibodies That Activate The EPO Receptor." *Experimental Hematology*, vol. 23, No. 8: p. 828, XP002044302; Aug. 1995, New York, NY, USA.
Hallgeir Rui Et Al.: "JAK2 Activation and Cell Proliferation Induced by Antibody–Mediated Prlocatin Receptor Dimerization," Endocrinology, vol. 135, No. 4: pp. 1299–1306, XP002044303, Oct. 1994, Philadelphia, PA, USA.
H. Schneider Et Al.: "Homodimerization of Erythropoietin Receptor by a Bivalent Monoclonal Antibody Triggers Cell Proliferation and Differentiation of Erythroid Precursors", Blood, vol. 89, No. 2: pp. 473–482, XP002044304, Jan. 1997, New York, NY,USA.
S. Elliott Et Al.: "Activation of the Erythropoietin (EPO) Receptor by Bivalent Anti–EPO Receptor Antibodies", The Journal Biological Chemistry, vol. 271, No. 40: pp. 24691–24697, XP002044305, Oct. 1996, Baltimore, MD, USA.

*Primary Examiner*—Nancy A. Johnson
*Attorney, Agent, or Firm*—Wayne W. Montgomery

[57] ABSTRACT

Antibodies and Bivalent molecules which activate erythropoietins and induce the proliferation or differentiation of erythroid progenitor cells are provided. Also provided are methods of using such bivalent molecules for drug discovery, diagnosis and treatment of disorders related to the activation of an erythropoietin receptor.

3 Claims, 4 Drawing Sheets

A

B

BaF3/EPO-R cells:

$K_A = 4.4 +/- 0.9 \times 10^6$ M$^{-1}$ $K_D = 228 +/- 47$ nM

UT-7/EPO cells:

$K_A = 1.9 +/- 0.2 \times 10^5$ M$^{-1}$ $K_D = 52 +/- 7$ nM

BIVALENT MOLECULES THAT FORM AN ACTIVATING COMPLEX WITH AN ERYTHROPOIETIN RECEPTOR

TECHNICAL FIELD

This application claims priority from provisional application Serial No. 60/059,063 which was converted from non-provisional application Serial No. 08/667,240, filed Jun. 21, 1996, and is directed to bivalent molecules that trigger cell proliferation and differentiation of erythroid precursors by activating signal transduction through the formation of a complex with erythropoietin receptors.

BACKGROUND

Erythropoietin (EPO), a 34-kDa glycoprotein hormone, is the major regulator of mammalian erythropoiesis (Krantz, S. B. (1991) *Blood* 77, 419–434). EPO acts on erythroid progenitor cells by preventing apoptosis (Koury et al. (1990) *Science* 248, 378–381; Zhuang et al. (1995) *J Biol Chem* 270, 14500–14504), stimulating proliferation of erythroid precursor cells and by inducing differentiation into mature erythrocytes. These effects are transduced by binding of EPO to a specific erythropoietin receptor (EPO-R) on the surface of committed erythroid progenitor cells (Youssoufian et al. (1993) *Blood* 81, 2223–2236). Deletion of EPO or EPO-R genes in mice has shown that EPO is crucial for the survival, proliferation and differentiation of late committed progenitors (colony forming unit-erythroid, CFU-E), but not of early progenitors (burst forming erythroid, BFU-E) (Wu et al. (1995) *Cell* 83, 59–67). Mice homozygous for a deletion of either EPO or EPO-R genes die during embryogenesis due to failure of erythropoiesis in the fetal liver.

The EPO-R is a member of the cytokine receptor type I superfamily, which includes the receptors for interleukins (IL) 2–7, granulocyte-macrophage colony-stimulating factor (GM-CSF), granulocyte-stimulating factor (G-CSF), growth hormone (GH), prolactin, thrombopoietin (TPO), leukemia inhibitory factor (LIF), and leptin (Bazan, J. F. (1990) *Proc. Natl. Acad. Sci.* 87, 6934–6938; Alexander et al. (1995) *EMBO J.* 14, 5569–5578; Tartaglia et al. (1995) *Cell* 83, 1263–1271).

Evidence for EPO induced receptor dimerization is based primarily on constitutively active EPO-R mutants, which contain point mutations introducing cysteine substitutions into the extracellular domain at amino acid positions R129, E132, and E133 (Longmore et al. (1991) *Cell* 167, 1089–102; Yoshimura et al. (1990) *Nature* 348, 647–649; Watowich et al. (1992) *Proc Natl Acad Sci USA* 89, 2140–2144; Watowich et al. (1994) *Mol Cell Biol* 14, 3535–3549; Longmore et al. (1994) *Mol Cell Biol* 14, 2267–2277). The EPO-R mutants form disulfide-linked homodimers in the endoplasmatic reticulum and on the cell surface (Watowich et al. (1992)). Based on sequence alignments with the related GH receptor, these mutations are expected to be in the receptor-dimer interface region. Expression of the constitutively active EPO-R (R129C) mutant in BaF3 cells results in factor-independent proliferation, and expression in primary cultures of mouse fetal liver cells induce EPO-independent erythroid differentiation (Pharr et al. (1993) *Proc Natl Acad Sci USA* 90, 938–942). Furthermore, mice infected with a retrovirus carrying the EPO-R (R129C) mutant develop erythroleukemia (Longmore et al. (1994)). Truncated signal transduction inactive receptor mutants lacking part of the intracellular signaling domain are dominant-negative when coexpressed with wild-type EPO-R (Watowich et al. (1994); Barber et al. (1994) *Mol Cell. Biol* 14, 2257–2265). Both wild-type and truncated receptors can be coimmunoprecipitated with an antibody directed against the C-terminus of the wild-type receptor, which is not present in the truncated form (Miura et al. (1993) *Arch Biochem Biophys* 306, 200–208), further suggesting the presence of receptor dimers on the cell surface.

Although dimerization of EPO-R is required, it is not sufficient for complete activation of cells. Other accessory cellular factors may be required to send a proliferation signal and, furthermore, these factors may be different from those required to send a differentiation signal. It is desirable to identify molecules other than EPO that activate the EPO-R and stimulate erythropoiesis and this invention meets that need.

SUMMARY OF THE INVENTION

An aspect of this invention is an antibody which activates erythropoietin receptors.

A second aspect of this invention is a bivalent molecule which activates erythropoietin receptors, which bivalent molecule contains at least one binding domain that selectively recognizes an epitope located on the extracellular domain of an erythropoietin receptor, which epitope is selectively recognized by the monoclonal antibody produced by Hybridoma #34.10.1 deposited at the ATCC as ATCC HB-12088.

A third aspect of this invention is a hybridoma cell line which produces a monoclonal antibody which activates erythropoietin receptors, which monoclonal antibody contains two binding domains that selectively recognizes an epitope located on the extracellular domain of an erythropoietin receptor, which epitope is selectively recognized by the monoclonal antibody produced by Hybridoma #34.10.1 deposited at the ATCC as ATCC HB-12088.

A fourth aspect of this invention is a method of treating a condition in a mammal in which diminished erythropoietin receptor activity contributes to the pathology and/or symptomatology of the condition, which method comprises administering to such animal a therapeutically effective amount of an antibody which activates erythropoietin receptors.

A fifth aspect of this invention is method of treating a condition in a mammal in which diminished erythropoietin receptor activity contributes to the pathology and/or symptomatology of the condition, which method comprises administering to such animal a therapeutically effective amount of a bivalent molecule which activates erythropoietin receptors, which bivalent molecule contains at least one binding domain that selectively recognizes an epitope located on the extracellular domain of an erythropoietin receptor, which epitope is selectively recognized by the monoclonal antibody produced by Hybridoma #34.10.1 deposited at the ATCC as ATCC HB-12088.

A sixth aspect of this invention is pharmaceutical composition comprising a therapeutically effective amount of an antibody which activates erythropoietin receptors in combination with a pharmaceutically acceptable excipient.

A seventh aspect of this invention is pharmaceutical composition comprising a therapeutically effective amount of a bivalent molecule which activates erythropoietin receptors, which bivalent molecule contains at least one binding domain that selectively recognizes an epitope located on the extracellular domain of an erythropoietin receptor, which epitope is selectively recognized by the monoclonal antibody produced by Hybridoma #34.10.1 deposited at the ATCC as ATCC HB-12088.

BRIEF DESCRIPTION OF THE DRAWINGS

The invention now being generally described, the same will be better understood by reference to the following detailed description of specific embodiments in combination with the figures that form a part of this specification.

FIG. 2B is a graph showing the dose-dependent cell proliferation of UT-7/EPO cells in the presence of various concentrations of MAb34 (open squares), control anti-Ax1 antibody unrelated to EPO (solid circles), and EPO (open triangles), respectively as described in Example 4. Experiments were done in duplicate.

DESCRIPTION OF SPECIFIC EMBODIMENTS

Figure 1:
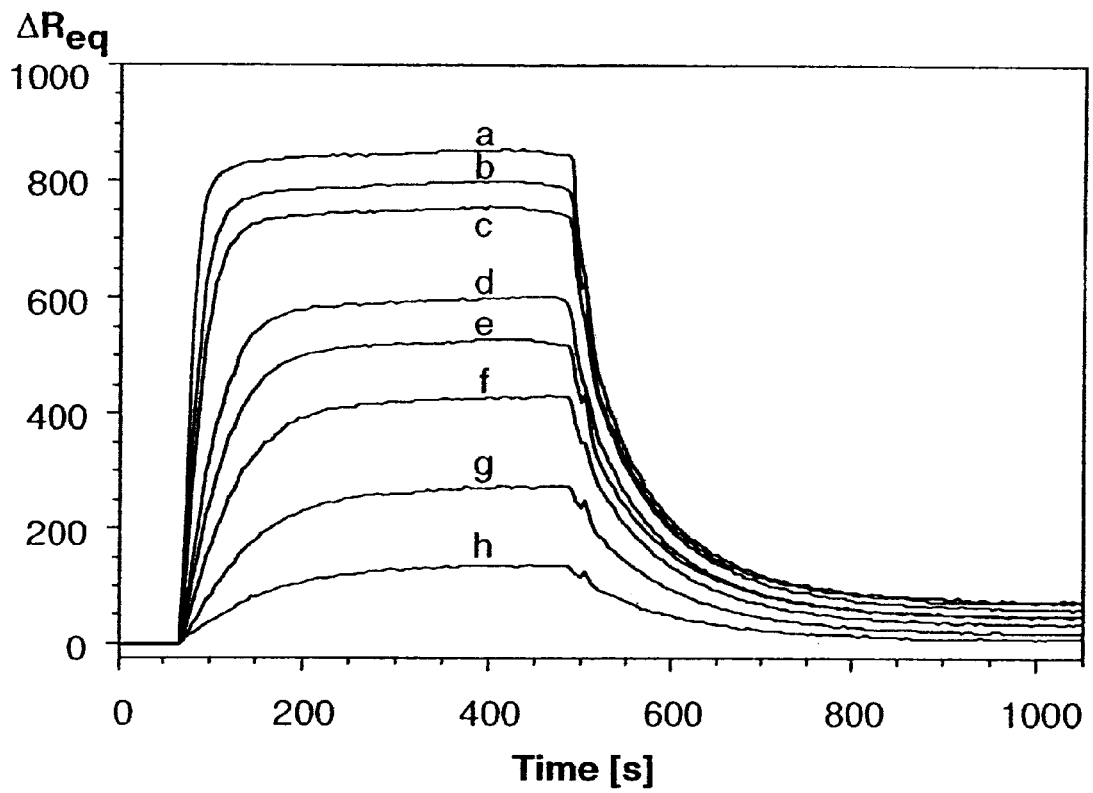
FIG. 1A is a BIAcore sensogram recording of various concentrations of EPObp (ranging from 10 to 1500 nM) injected over immobilized MAb34, corrected by data from control surfaces. Data from 8 representative EPObp concentrations from a total of 16 are shown.
Figure 1:
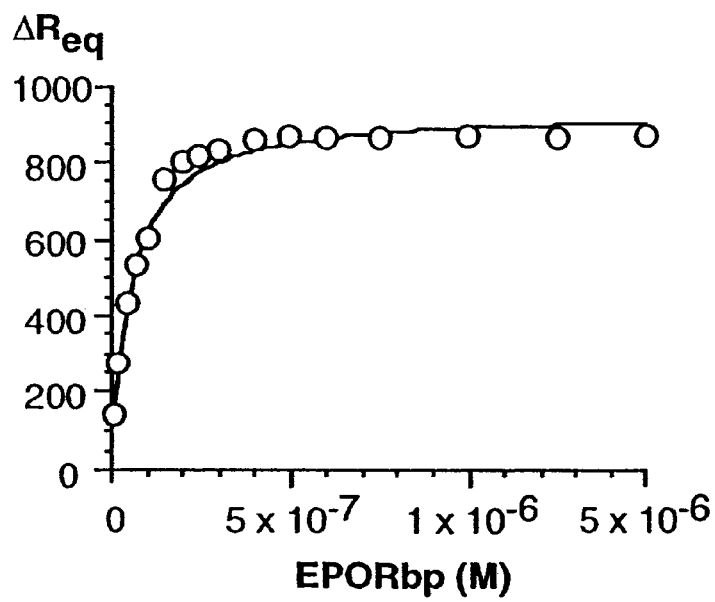

EPO stimulates proliferation and differentiation of erythroid progenitor cells. Homodimerization of EPO-R by EPO on the cell surface is believed to be the key event in receptor activation and subsequent signal transduction (Youssoufian et al.). Bivalent molecules that possess two identical binding sites for a given region on the extracellular domain of EPO-R, such as antibodies, for example, can bind two EPO-R molecules thereby bringing them into close proximity to permit dimerization. These bivalent molecules must bind so as to activate the signal transduction pathway and it is desirable that such activation result in both proliferation and differentiation of erythroid progenitors. It is also possible for the binding domains of the bivalent molecules to recognize different regions of EPO-R and have a similar or an enhanced effect. Such bivalent molecules are useful for researching the mechanism of EPO-R activation and signal transduction and have therapeutic and diagnostic applications as well.

Definitions

"Purified" means that the monoclonal antibody is separated from at least some of the proteins normally associated with the monoclonal antibody and preferably separated from all cellular materials other than proteins.

"Epitope" means a region of an EPO-R recognized by a first antibody wherein the binding of the first antibody to the region prevents binding of a second antibody or other bivalent molecule to the region. The region encompasses a particular core sequence or sequences selectively recognized by a class of antibodies and can include additional EPO-R sequences. For example, several antibodies can selectively bind to the sequence XYZ and although they may bind with differing affinities to abcXYZ than to XYZdef, they are nevertheless binding to the same epitope. The epitope can be contiguous or non-contiguous such that the first antibody selectively recognizes a peptide fragment containing the core sequence XYZ, but the second antibody or other bivalent molecule selectively recognizes a fragment containing the core sequence only in its native conformation on the EPO-R. For example, the tertiary structure of the EPO-R can give rise to the epitope pqrXYZ from the primary sequence of pqr . . . XYZ. An antibody specific for pqrXYZ would not be expected to bind the peptide pqr . . . XYZ as effectively as it would the EPO-R itself, yet it will selectively recognize either the peptide fragment or the EPO-R. Thus, abcXYZ, XYZdef, and pqrXYZ are all the same epitope because they share the same core sequence. The core sequence comprises at least 3 amino acid residues, preferably 4–20 amino acid residues, and can comprise as many as 35 amino acid residues. Thus, the "MAb34 epitope" is an epitope that is selectively recognized by the MAb34 antibody described in more detail below.

"Selectively recognizes" or "selectively recognized" means that binding of the antibody or other bivalent molecule to an epitope is at least 2-fold greater, preferably 2–5 fold greater, and most preferably more than 5-fold greater than the binding of the bivalent molecule to an unrelated epitope or than the binding of an unrelated bivalent molecule to the epitope, as determined by techniques known in the art and described herein, such as, for example, ELISA and cold displacement assays.

"Bivalent molecule" or "BV" means a molecule capable of binding to two separate erythropoietin receptors at the same time, thereby forming a molecular complex. The bivalent molecule is not limited to having two and only two binding domains and can be a polyvalent molecule or a molecule comprised of linked monovalent molecules so long as at least two EPO-R binding domains are provided. The binding domains of the bivalent molecule can selectively recognize the same epitope or different epitopes located on the EPO-R extracellular domain, so long as at least one binding domain selectively recognizes an epitope recognized by MAb34 (i.e., the MAb34 epitope) and the resultant (EPO-R)$_2$:BV complex is active in signal-transduction. The bivalent molecule can be proteinaceous or non-proteinaceous provided that it can form a complex sufficiently stable to activate the EPO-R or to be detected. The binding domains can be linked in any of a number of ways including, but not limited to, disulfide bonds, peptide bridging, amide bonds, and other natural or synthetic linkages known in the art (Spatola et al., "Chemistry and Biochemistry of Amino Acids, Peptides and Proteins," B. Weinstein, eds., Marcel Dekker, New York, p. 267 (1983) (general review); Morley, J. S., "Trends Pharm Sci" (1980) pp. 463–468 (general review); Hudson et al., *Int J Pept Prot Res* (1979) 14, 177–185; Spatola et al., *Life Sci* (1986) 38, 1243–1249; Hann, M. M., *J Chem Soc Perkin Trans I* (1982) 307–314; Almquist et al., *J Med Chem* (1980) 23, 1392–1398; Jennings-White et al., *Tetrahedron Lett* (1982) 23, 2533; Szelke et al., European Application EP 45665; Chemical Abstracts 97, 39405 (1982); Holladay, et al., *Tetrahedron Lett* (1983) 24, 4401–4404; and Hruby, V. J., *Life Sci* (1982) 31, 189–199).

"Proteinaceous" means the molecule referred to comprises a polypeptide sequence. Thus a proteinaceous molecule can be comprised entirely of polypeptide sequences or it can comprise one or more non-peptidic substituents in addition to polypeptide sequences.

"Therapeutically effective amount" means an amount that provides a therapeutic effect for a given condition and administration regimen. In the present invention, the therapeutic effect is an increase in erythrocyte levels, which can be evidenced by a rise in hematocrit in the patient being treated.

"Treating", as in treating a condition, means (1) preventing the condition from occurring in a mammal which may be predisposed to the condition but does not yet experience or display symptoms of the disorder, (2) inhibiting the condition (e.g., arresting development of the condition) or (3) ameliorating the condition (e.g., causing regression of the disorder).

"Pathology of a condition" means the essential nature, causes and development of the condition as well as the structural and functional changes that result from the disease processes.

"Symptomatology of a condition" means any morbid phenomenon or departure from the normal in structure, function or sensation experienced by the patient and indicative of the condition, their production and the indications they furnish.

In one aspect of the invention an antibody is provide that selectively recognizes the extracellular domain of the erythropoietin receptor to form a molecular complex active in signal transduction. In particular, it should be noted that the invention is not limited to use or identification of the specific monoclonal described in the Examples section below. Any antibody that selectively recognizes an epitope and that results in homodimerization of the erythropoietin receptor and subsequent cell proliferation and differentiation of erythroid precursors is encompassed by the present invention. Use of such antibodies is easily accomplished by one of ordinary skill in the art given the teachings of the present specification.

In another aspect of the invention a bivalent molecule (BV) is provided that selectively recognizes the extracellular domain of the erythropoietin receptor. The bivalent molecule can bind the extracellular domains of two erythropoietin receptor to form a molecular complex active in signal transduction. In particular, it should be noted that the invention is not limited to use or identification of the specific monoclonal described in the Examples section below. Any bivalent molecule as defined above that selectively recognizes an epitope selectively recognized by monoclonal antibody MAb34 (MAb34 epitope) and that results in homodimerization of the erythropoietin receptor and subsequent cell proliferation and differentiation of erythroid precursors is encompassed by the present invention. Use of such molecules is easily accomplished by one of ordinary skill in the art given the teachings of the present specification.

The bivalent molecule can have a detectable label attached thereto, such as a fluorescent label (e.g., fluorescein, isothiocyanate (FITC)), an affinity label (e.g., biotin), an enzymatic label (e.g., horseradish peroxidase or alkaline phosphatase), or an isotopic label (e.g., $^{125}I$) or any other such detectable moiety. Apart from the ability of the bivalent molecules of the invention to modulate erythroid precursor proliferation and differentiation, these molecules are also useful for the detection of the presence or absence of erythropoietin receptors in a sample.

A preferred bivalent molecule is an antibody that selectively recognizes the MAb34 epitope located on the extracellular domain of the erythropoietin receptor. Antibodies can be produced by the immunization of various animals, including mice, rats, rabbits, goats, primates, humans and chickens with EPO-R or peptide fragments of EPO-R containing the MAb34 epitope. Preferably, the protein is purified prior to immunization of the animal. The EPO-R can be purified by methods known in the art, for example, gel filtration, ion exchange, affinity chromatography, etc. The EPO-R can be naturally occurring or genetically engineered as is apparent to one of ordinary skill in the art. Preferably the antibody is purified. Affinity chromatography or any of a number of other techniques known in the art can be used to isolate polyclonal or monoclonal antibodies from serum, ascites fluid, or hybridoma supernatants.

The antibody can be of the isotypes IgA, IgE, IgM, preferably is an IgG antibody, and can be an IgD antibody, although this is less preferred. IgG subclasses include IgG1, IgG2a, IgG2b and IgG3 in the mouse; IgG1, IgG2a, IgG2b, and IgG2c in the rat; and IgG1, IgG2, IgG3 and IgG4 in the human. Useful antibodies of the invention are chosen upon consideration of such factors as complement fixation, autoaggregation, ability to mediate mast cell degranulation, ability to bind Fc receptors or macrophage receptors and resistance to proteolytic enzymes. Preferably, the bivalent molecules of the invention are resistant to proteolytic cleavage and are not excessively immunogenic. Also included are fully human antibodies selectively recognizing the MAb34 epitope produced in genetically altered mice (PCT Application No. 93/122227).

Preferably, the antibody is a monoclonal antibody. Methods of generating monoclonal antibodies are known in the art and are described in detail, for example, by Oi and Herzenberg in "Selected Methods in Cellular Immunology" (1979) (B. B. Mishell and S. M. Shiigi, eds.), San Francisco: W. J. Freeman Publishers, pp. 351–352. In short, after immunization of an animal spleen cells are isolated and fused with myeloma cells, such as mouse myeloma cell lines P3X63Ag8.653 (ATCC CRL 1580); P3-NS1/1Ag 4; and S194/5, XXO, BUI; human fusion partners such as UV 729-6 and SKO-007; and mouse-human hetero-myeloma lines, such as SHM-A6 and SHM-D33 (PCT Application No. 81/00957; Schlom et al., *Proc. Natl. Acad. Sci. USA* (1980) 77, 6841–6845; Croce et al. (1980) *Nature* 288, 488–489). The fusion is carried out in the presence of a non-ionic detergent for a short period of time and removed. The cells are then subjected to selective conditions, such as HAT and ouabain, for example, that are cytotoxic to the parent cells, but not fused hybrid cells. Such hybridoma cell lines are also encompassed by the invention and provide an inexhaustive supply of monoclonal antibody. Typically, antibody titers are determined by methods such as enzyme linked immunosorbent assays (ELISA) (Engrall (1977) *Med. Biol.* 55, 193–200)to determine their affinity for their binding partners. The ability of the antibodies to activate EPO-R can be determined by cell proliferation or differentiation assays, some of which are described herein.

A preferred monoclonal antibody is MAb34, which is deposited at the ATCC as Hybridoma #34.10.1 assigned ATCC HB-12088. The monoclonal antibody Mab34 directed against the extracellular domain of the EPO-R that activates EPO-R by dimerization and thus mimics EPO action as is demonstrated below in Example 4. This bivalent IgG antibody triggers the proliferation of EPO-dependent cell lines and induces differentiation of erythroid precursors in vitro. Activation of cell proliferation and differentiation show a bell-shaped response curve over the range of antibody concentration tested with a maximum occuring at MAb34 concentrations in close vicinity to its $K_D$. Indeed, a mathematical model (Perelson, A. S. (1984) in *Cell Surface Dynamics: Concepts and Models* (Perelson, A. S., DeLisi, C., and Wiegel, F. W., eds), pp. 223–276, Marcel Dekker, Inc., New York, N.Y.) predicts that a maximum of 2:1 receptor/antibody complexes is formed at a concentration of $0.5 \times K_D$.

The mechanism of receptor activation by homodimerization implies that at high concentrations the formation of 1:1 receptor/ligand complexes is favored over 2:1 complexes, thereby turning the ligand agonist into an antagonist. Thus, EPO and MAb34 should self-antagonize at high concentrations in both cell proliferation and differentiation assays. Example 4 demonstrates that EPO and MAb34 antagonize ligand-dependent cell proliferation with $IC_{50}$ concentrations of approximately 20 $\mu$M and 2 $\mu$M, respectively. We have further analyzed the MAb34:EPO-R interaction using a mathematical model describing antibody mediated receptor dimerization. The predicted receptor dimer formation on the cell surface was consistent with the observed proliferation and differentiation activity data.

Although one of ordinary skill in the art would expect that all bivalent antibodies specific for the extracellular domain should dimerize the receptor, the vast majority of antibodies specific to the EPObp in our screen are not active (47 out of 48) and form inactive complexes (see Example 2). Surprisingly, MAb34 does not bind to the EPO binding site of the erythropoietin receptor as determined by competition with EPO in a cold displacement assay. Thus, the bivalent molecules of the invention have revealed a new site of erythropoietin receptor interaction not previously known to trigger receptor activation and signal transduction.

Another preferred monoclonal antibody is a high-affinity variant of MAb34. Such variants can be prepared by a number of methods known in the art or developed in the future, including the random or site-directed mutagenesis of the variable region of MAb34. For example, degenerate oligonucleotides can be substituted for the variable region in MAb34 and the resultant antibody population screened by competition with MAb34 for EPO-R binding. As described further below, phage display can also be utilized for this purpose.

The antibody can be a chimeric antibody such as a humanized antibody or a CDR-grafted antibody in which regions other than the binding domains are replaced with human immunoglobulin polypeptide sequences (U.S. Pat. Nos. 4,816,567 and 5,225,539). Another preferred chimeric antibody is a bispecific antibody in which one of the binding domains selectively recognizes an epitope located on the extracellular domain of EPO-R other than the MAb34 epitope, provided that the chimeric antibody can form an $(EPO-R)_2$:antibody complex active in signal transduction, a property possibly dependent upon the distance and geometry of the receptors.

Another preferred aspect is a bivalent proteinaceous molecule other than an antibody comprising two binding domains that selectively recognize the MAb34 epitope. For example, peptides can be designed based on an analysis of the amino acid sequence of the complementarity-determining region (CDR) of MAb34. A bivalent molecule can be synthesized containing two or more of such peptides linked or fused to each other and possibly to an additional polypeptide structure provided as a scaffold for stability or some other purpose such as, for example, the recruitment of a tertiary molecule. Alternatively, random peptide libraries prepared by techniques known in the art, such as, for example, peptide chemistry, phage display (Ladner et al; Huse; Devlin; Dower et al.; Markland et al.) or the yeast two-hybrid system can be screened by competitive inhibition of MAb34 binding to EPO-R to identify a polypeptide sequence that selectively binds to the MAb34 epitope. This peptide can then be synthesized in a bivalent form and tested for an ability to activate EPO-R by any of the methods herein described, known in the art, or developed in the future.

The bivalent proteinaceous molecule can be a bispecific molecule in which one of the binding domains selectively recognizes an epitope located on the extracellular domain of EPO-R other than the MAb34 epitope, such as, for example, an epitope corresponding to the EPO-binding domain. The bispecific molecule can be a bispecific antibody as mentioned above, a chimeric molecule comprising an immunoglobulin portion and a non-immunoglobulin portion, or an entirely non-immunoglobulin proteinaceous bispecific molecule, so long as the bispecific molecule is capable of forming an active molecular complex with EPO-R.

Another preferred aspect is a non-proteinaceous bivalent molecule. Such a molecule can be identified and produced by techniques known in the art, such as, for example, peptidomimetics. Such mimetics can be produced by rational drug design based on molecular modeling and the polypeptide sequence of the CDR of MAb34. Alternatively, combinatorial chemical libraries can be screened by competitive inhibition of MAb34 binding to EPO-R to identify a compound that selectively binds to the MAb34 epitope and then the compound can be synthesized in a bivalent form and tested for its ability to form an active $(EPO-R)_2$:BV complex by any of the methods herein described.

Bivalent molecules selectively recognizing the MAb34 epitope can be produced in a number of methods using techniques known in the art. These methods are not part of the invention but are provided herein for the convenience of the reader. One method is initially to screen a population of candidate molecules for an ability to compete with MAb34 for binding of EPO-R, and then to perform a functional determination of an ability to activate EPO-R, such as, for example, thymidine uptake proliferation assays, erythroid cell differentiation assays, or any assays exploiting steps in the signal transduction cascade. Suitable assays are provided for illustrative purpose in the Examples section. Another method is to synthesize peptides corresponding to the MAb34 epitope for use as a binding partner in binding assays. The MAb34 epitope can be mapped by preparing overlapping synthetic peptides that span the extracellular domain EPO-R and screening them for binding to MAb34. Another procedure that can be used for mapping the MAb34 epitope is phage display (Ladner et al., PCT Application No. PCT/US92/01456; Huse, PCT Application No. PCT/US91/07141; Devlin, PCT Application No. PCT/US91/03332; Dower et al., PCT Application No. PCT/US91/02989 and PCT/US91/04384; Markland et al., PCT Application No. PCT/US92/01539) whereby bacteriophage displaying random peptide sequences on the phage surface are screened by binding to immobilized MAb34 and the peptide sequences are subsequently deduced from the polynucleotide sequence obtained from nucleic acid sequencing.

The invention also provides an $(EPO-R)_2$:BV complex. Such a complex, when present on the surface of a cell, is useful for modulating proliferation and differentiation of erythroid precursor cells. Such a complex, whether present on the surface of a cell or isolated from other cellular components, can also be used for EPO-R activator drug discovery where compounds that are potential candidate drugs for the treatment of disorders treatable by EPO-R activitation are screened as described above for their ability to competitively inhibit complex formation between EPO-R and previously identified bivalent molecules of the invention.

In another preferred embodiment, the invention provides methods and kits for detecting the presence or absence of an erythropoietin receptor or an activatable EPO-R in a biological sample. In a preferred aspect, the detection is achieved by a binding assay in which the level of binding of a bivalent molecule to EPO-R is detected. Basically, the biological sample is contacted with the bivalent molecule and the level of binding is detected. Many similar assays are well known in the art and include, but are not limited to, ELISA's, binding displacement assays, binding competition assays, BIAcore (Pharmacia Biosensor) analysis, radioimmunoassays, enzyme-linked immunoassays, Western immunoblot assays and the like. The biological samples include tissue specimens, intact cells, or extracts thereof. Antibodies may be used as part of a diagnostic kit to detect the presence of EPO receptors in a biological sample. Such kits employ bivalent molecules, preferably a monoclonal antibody, having an attached label to allow for detection.

The detection can also be achieved by a functional assay in which it is the activation of the receptor that is detected. For example, any of a number of cellular products of the signal transduction cascade triggered by EPO-R activation can be monitored in a functional assay, such as nitric oxide, prostaglandins, cAMP, cGMP, $Ca^{2+}$, inositol phosphates and the like. Alternatively, kinase and phosphatase activities resulting from EPO-R activation can also be monitored in a functional assay. Such methods can be used in the diagnosis of anemia and other diseases characterized by a dysfunctional EPO-R or otherwise related to EPO-R activation.

The invention also provides methods of modulating the endogenous activity of an erythropoietin receptor in a mammal. Typically activation of the EPO-R in an erythroid precursor cell results in cell proliferation or differentiation. Such methods are useful for treating disorders characterized by low erythrocyte levels. Thus, any condition treatable with EPO, such as anemia, for example, is amenable to treatment with the bivalent molecules of the invention. Any of the bivalent molecules of the invention can be used for this purpose, subject to such considerations as variations in bioavailability, antigenicity, and potency among the different bivalent molecules. For example, MAb34 may be more potent than another antibody, but for long-term use, a slightly less potent humanized antibody may be preferred. Other non-immunoglobulin bivalent molecules may be preferred where stability or the need for an orally active drug is an issue. The amount and method of administering the therapeutic molecules of the invention can be ascertained by one skilled in the art. Preferably, administration of large bivalent molecules is by injection, whether subcutaneous, intramuscular, or intravenous. Smaller, less peptidic bivalent molecules can be administered orally as well as intravenously.

The invention also provides a pharmaceutical composition comprising a therapeutically effective amount of the bivalent molecule of the invention in a pharmaceutically acceptable adjuvant, which can be selected from one or more of a diluent, carrier, preservative, emulsifier, anti-oxidant and/or stabilizer. Pharmaceutically acceptable adjuvants are known to one skilled in the art (Remington's Pharmaceutical Sciences, 18th ed. A. R. Gennaro, ed. Mack, Easton, Pa. (1990)).

EXAMPLES

The invention now being generally described, the same will be better understood by reference to the following detailed examples, which are provided for the purpose of illustration only and are not to be considered limiting of the invention unless otherwise specified.

Example 1

Generation of EPO-R Monoclonal Antibodies

In order to obtain an antibody capable of dimerizing an EPO-R, monoclonal antibodies were raised against the extracellular, ligand binding domain of the human EPO-R (EPObp).

Expression and Affinity Purification of Soluble Human EPO-R

DNA encoding a soluble truncated EPObp was generated by the polymerase chain reaction (PCR) using the full-length cDNA as template. The amplification product introduces a TAG termination codon 5' of the transmembrane region and encodes the extracellular domain comprising amino acids 1 through 249 of the published sequence (Jones et al. (1990) *Blood* 76, 31–35). The PCR product was subcloned into expression vector pRc/CMV (Invitrogen) and stably transfected into CHO cells. Individual clones secreting EPObp were selected by limiting dilution cloning. Roller bottles (surface area 1,700 $cm^2$, Corning, Corning, N.Y.) were seeded with the stable cell line and grown to confluence in RPMI plus 10% FBS. Cells were washed twice in serum free RPMI medium and cultured in 200 ml of serum-free RPMI. Cell supernatant was collected after two days and fresh medium was added for another two days. The EPObp was secreted at an approximate concentration of 0.2 µg/ml and was purified by EPO affinity chromatography.

EPO was oxidized with 10 mM $NaIO_4$ and biotinylated using 10 mM biotin hydrazide (Pierce) following the manufacturer's instructions. A ligand affinity column was prepared by immobilizing biotinylated EPO (10 mg) on Streptavidin 3M Emphaze beads (3 ml; Pierce), overnight in Dulbecco's phosphate buffered saline (PBS, Irvine Scientific) at 4° C. The beads were separated from the supernatant by centrifugation, and incubated with 10 mM biotin in PBS for 2 h at 4° C. to saturate all biotin binding sites. After washing with PBS, the EPO coated beads were packed in a glass column (Omnifit). Cell supernatant (10 L) was concentrated and diafiltered to 1 L in 20 mM Tris HCl, pH 7.6 and loaded on the column at a flow rate of 0.7 ml/min. The column was washed with 50 ml of 20 mM Tris/HCl, pH 7.6. Bound EPObp was eluted with 750 mM NaCl in 20 mM Tris/HCl, pH 7.6. SDS-PAGE analysis showed a single 30 kD EPObp band. The EPObp fractions were pooled, concentrated and buffer exchanged with PBS to a final concentration of 0.8 mg/ml.

Generation of Monoclonal Antibodies and Screening for Binding to EPObp

Monoclonal antibodies were generated essentially as described in Galfré et al. (1981) *Methods. Enzymol.*, 73, 3–46). Five Balb/c mice were immunized by seven subcutaneous injections at two sites over a period of 14 weeks. Each 50 µl injection contained 25 µg EPObp in Freud's adjuvant.

Antibody titers were measured by ELISA after 12 weeks. Polysorb microtiter plates (Nunc, Roskilde, Denmark) were incubated with 5 µg/ml EPObp in PBS for 1 h at 37° C., washed and then blocked with 20 mg/ml bovine serum albumin (BSA) in PBS for 1 h at 37° C. Serial dilutions of sera samples in PBS, 1 mg/ml BSA, 0.05% Tween-20 were added and incubated for 1 h at 37° C. After washing, the plates were incubated with a sheep anti-mouse IgG coupled to horseradish peroxidase (HRP; Sigma, St. Louis, Mo.) at 0.1 ng/ml in PBS containing 1 mg/ml BSA, 0.02% Tween-20 for 1 h at 37° C. Plates were then washed and 100 µl TMB/$H_2O_2$ developing solution (Pierce, Rockford, Ill.) was added and incubated for 5 min. Color development was stopped by adding 100 μl 1M sulfuric acid, and the $OD_{450-650}$ was determined (Molecular Devices). The titers ranged from 10,000 to 50,000.

A final injection of 150 μg EPObp was given to the mouse expressing the highest antibody titer. After 3 d, spleen cells were isolated and fused with myeloma strain P3XAg8.653 (ATCC CRL 1580) to generate 475 hybridomas. After selection in HAT medium (Littlefield (1964) *Science* 145, 709–710) for 10 days, supernatants were screened for specific antibody production by ELISA.

Because a low number of agonist antibodies is expected, two different methods for immobilization of the EPObp were used to ensure identification of a maximum number of EPObp MAb's. In ELISA #1, EPObp was covalently immobilized. EPObp was oxidized in 1 mM $NaIO_4$, 50 mM sodium acetate, pH 5.5 at 4° C. for 30 min in the dark. The protein was separated from periodate on a NAP-5 column (Pharmacia Biotech Inc., Piscataway, N.J.) and incubated on hydrazide-activated microtiter plates (Unisyn, San Diego, Calif.) at 2 μg/ml (100 μl per well) for 1 h at room temperature. Plates were blocked with PBS, 20 mg/ml BSA for 1 h. In ELISA #2 EPObp was immobilized via MAb 2E12, a specific, non-neutralizing rat monoclonal antibody directed against EPObp: Polysorb microtiter plates were incubated with 10 μg/ml MAb 2E12 for 1 h at 37° C., washed and blocked with PBS containing 20 mg/ml BSA for 1 h at 37° C. EPObp (1 μg/ml) was added in PBS, 1 mg/ml BSA, 0.02% Tween-20 for 1 h at 37° C. After the immobilization of EPObp, both ELISA protocols were identical. Hybridoma supernatants were added and incubated for 1 h at 37° C. After washing, bound antibodies were determined using anti-mouse IgG—HRP conjugate as described above. A total of 48 supernatants were found to bind to immobilized EPObp in at least one out of the two ELISA assays and were further screened for agonist activity.

Example 2

Screening of EPO-R Monoclonal Antibodies for Receptor Agonist Activity

To identify a monoclonal antibody capable of inducing cell proliferation, positive clones were transferred to 24-well microtiter plates, and supernatants were assayed in a thymidine uptake proliferation assay using the cell line BaF3/EPO-R and the parental BaF3 as a control. BaF3 cells transfected with a full-length human EPO-receptor can grow in media containing either IL-3 or human EPO.

Development of an EPO-Dependent BaF3/EPO-R Cell Line

An EPO-dependent BaF3/EPO-R cell line was generated by transfecting the full-length human EPO receptor into BaF3 cells, a murine IL-3 dependent cell-line (Palacios et al. (1985) *Cell* 41, 727–734). A cDNA encoding the full-length human EPO receptor (Winkelmann et al. (1990) *Blood* 76, 24–30; Jones et al. (1990) *Blood* 76, 31–35) was cloned into plasmid expression vector pRc/CMV (Invitrogen, San Diego, Calif.). After electroporation into BaF3 cells, the cells were cultured in RPMI 1640 medium containing IL-3 for 2 days. Cells were washed twice, transferred into RPMI 1640 plus 135 pM EPO, and selected for EPO-dependent growth. Individual clones were selected by limited dilution cloning. The EPO-dependent cell line chosen for this study proliferates in the presence of EPO with an $EC_{50}$ of 15 pM. Scatchard analysis revealed 800 receptors per cell binding EPO with 300 pM affinity, assuming single site binding. Cells were maintained in RPMI 1640 with 10% fetal bovine serum (FBS), 20 mM HEPES pH 7.8, and 10 mM mercaptoethanol supplemented with 100 pM EPO. BaF3 cells were supplemented with 10% IL-3 containing WEHI-3B conditioned medium.

Thymidine Uptake Proliferation Assays

BaF3/EPO-R and IL-3-dependent BaF3 parental cells were incubated with individual hybridoma supernatants in the absence of EPO and IL-3, respectively, and proliferation was measured by [$^3$H]thymidine incorporation. BaF3 and BaF3/EPO-R cells were grown to late logarithmic phase, collected by centrifugation, washed three times with RPMI 1640 media (containing 10% FBS and 10 mM HEPES pH 7 in the absence of EPO and IL-3), then starved in the same media for 2 hours. Antibody test samples (hybridoma supernatants or purified proteins) were diluted at least 4-fold into 100 μl media and 100 μl cells were added (25,000 cells per well). EPO was dialyzed against 10 mM HEPES pH 7.0, and 100 μl test samples were combined with 100 μl cells (25,000 cells per well) in 2-fold concentrated medium. Plates were incubated for 4 hours at 37° C. and 5% $CO_2$ in a humidified tissue culture incubator. Then 0.5 μCi [$^3$H]thymidine (Amersham), diluted into 20 μl medium, was added and incubation continued for another 15 hours. Cells were harvested onto glass fiber filtermats using a Tomtec cell harvester (Wallac Oy), and incorporated radiolabel was determined using a Microbeta 1450 scintillation counter (Wallac, Turku, Finland).

The hybridoma supernatant of MAb clone 34 stimulated thymidine uptake in BaF3/EPO-R cells but not in BaF3 cells, indicating that the proliferation was specific to the presence of EPO-R. Hybridoma clone MAb34 was subcloned twice by limiting dilution. Ig-isotyping was performed using an IsoStrip Mouse Monoclonal Antibody Isotyping Kit from Boehringer Mannhelm (Indianapolis, Ind.). MAb34 is an IgG monoclonal which was subtyped as IgGα1.

Example 3

Purification and Determination of Binding Characteristics of an EPO-R Agonist To further characterize the binding characteristics of MAb 34 for an erythropoietin receptor, MAb34 was purified and used in cold displacement binding assays. Binding kinetics were examined using the BIAcore system. MAb34 was purified by protein G affinity chromatography, and Fab fragments (Fab34) were prepared by papain cleavage. 0.75 ug and 1.5 ug of EPObp was heat-denatured and analyzed by reducing SDS-PAGE on a 12% acrylamide gel and subsequent transfer to nitrocellulose. The blot was incubated with MAb34 (10 μg/ml) and subsequently with anti-mouse IgG coupled to horseradish peroxidase. A robust signal was obtained for both 0.75 ug and 1.5 ug samples of EPObp. This immunoblot analysis of heat-denatured and reduced EPObp suggested that MAb34 recognizes a linear continuous epitope.

Purification of Mab34

Hybridomas were grown in 47.5% RPMI, 47.5% DMEM, 5% FBS. Culture supernatant was filtered through a 0.2 μm membrane. A 6 ml protein G Sepharose 4 fast flow column (Pharmacia) was packed at 80 psi pressure. A 1 l sample was loaded at 4 ml/min at 4° C., followed by washing with >5 column volumes of PBS. MAb34 was then eluted from the column with ImmunoPure IgG elution buffer (Pierce) at 2 ml/min. The eluate was immediately neutralized to pH 7.5 by adding 3 M Tris. The purity was evaluated by non-reducing SDS-PAGE. $F_{ab}$ fragments were generated by papain cleavage using ImmunoPure IgG1 $F_{ab}$ Preparation Kit (Pierce) following the manufacturer's instructions. The F$_{ab}$ was further purified by gel filtration, using a Superdex 75 column (1.6 cm×60 cm, Pharmacia), eluted with PBS, and analyzed for purity by SDS-PAGE.

EPO Cold Displacement Assay

OCIM1 cells, a human erythroleukemia cell line which expresses EPO-R on the cell surface (Broudy et al. (1988) *Proc. Nat. Acad. Sci. USA* 85, 6513–6517), were grown in IMDM, 10% FBS, 1% penicillin-streptromycin-fungisone to approximately 2–5×10$^5$ cells/ml. Cells were collected by centrifugation, washed two times in binding buffer (RPMI 1640, 1% BSA, 25 mM HEPES pH 7.3), then resuspended in binding buffer containing 0.1% sodium azide and 10 μg/ml cytochalisin B at 1–2×10$^9$cells/ml. Cells (100 μl) in 96 well tissue culture plates were then incubated with 10 μl sample and 10 μl [$^{125}$I]-EPO (Amersham high specific activity; 3000 Ci/mmol, 2 mCi/ml) in a humidified tissue culture incubator at 37° C. After 3 h, cells were centrifuged through phthalate oil (60:40 (v/v) dibutyl/dinonyl phthalate) in titer tubes. The tubes containing cell pellets were quick frozen in a dry ice-ethanol bath and the cell pellet was clipped and then counted in a LKB 1277 gammamaster automatic gamma counter (Pharmacia).

MAb34 did not compete with [$^{125}$I]-EPO for binding to EPO-R in a displacement assay using human OCIM1 cells (Broudy et al. (1988) *Proc. Nat. Acad. Sci. USA* 85, 6513–6517), indicating that the binding sites of EPObp for EPO and for MAb34 are different.

Analysis of MAb34 and Fab34 Binding Kinetics

The binding kinetics of both the MAb34 and Fab34 to the EPObp were characterized using surface plasmon resonance. For MAb34 kinetics the antibody was immobilized to avoid avidity effects. For Fab34 kinetics, we immobilized EPObp.

Kinetic parameters for the interaction of MAb34 and its Fab fragment (Fab 34) with EPObp were measured by using real-time biospecific interaction analysis (BIAcore) (Johnsson et al. (1992) *Adv. Biosens.* 2, 291–336). The BIAcore system, CM-5 sensor chip, and reagents were from Pharmacia Biosensor, Piscataway, N.J. All injections on the sensor chip surface were at a flow rate of 5 ml/min and 25° C. unless otherwise stated. Between injections of reagents, the sensor chip was continuously washed with 10 mM HEPES, pH 7.5, 150 mM NaCl, 3.4 mM EDTA and 0.005% surfactant P$_{20}$. The interaction of MAb34 with EPObp was characterized by coupling approximately 6800 resonance units (RU) of MAb34 to the sensor chip surface using standard amine immobilization chemistry (Johnsson et al. (1991) *Anal Biochem.* 198, 268–277). Samples of EPObp ranging in concentration from 10–1500 nM were injected for 7 minutes over the MAb34 surface and over a control flow cell. After each injection of EPObp, a 1 minute pulse of 1 M formic acid was used to regenerate the MAb34 surface. To measure the interaction of EPObp and Fab34, oxidized EPObp (app. 500 RU) was immobilized via carbohydrazide coupling to the carboxymethylated dextran matrix (Karlsson et al. (1991) *J. Immunol. Methods* 145, 229–240). Injections of Fab34 spanned a concentration range of 1–500 nM. After each injection of Fab34, the EPObp surface was regenerated with a 50 ml pulse, at 50 ml/min, of 10 mM CAPS pH 10.4. Transformation and analysis of data were performed with BIAevaluation software (Pharmacia Biosensor, Piscataway, N.J.). Dissociation rate constants were determined by measuring dissociation of bound analyte in buffer flow. To minimize potential rebinding effects, only the initial 15 s of each dissociation profile was used for calculation of the dissociation rate constant.

Determinations of affinity were made from steady state equilibrium measurements and k$_a$ was inferred from the relationship K$_D$=k$_d$/k$_a$. Although determination of dissociation rate constants (k$_d$) was straightforward using the BIAevaluation software provided by the manufacturer, direct measurements of association rate constants (k$_a$) were severely hindered by mass transport limitations. Hence, the steady state (R$_{eq}$) binding values were used to calculate the affinity of the interaction (FIG. 1) (Karlsson et al.). The affinity constants calculated for MAb34 and Fab34 are summarized in Table 1. Both bind to the EPObp with an affinity of approximately 50 nM.

TABLE 1

| immobilized molecule | analyte | k$_a$ [M$^{-1}$s$^{-1}$] | k$_d$ [s$^{-1}$] | K$_D$ [nM] |
| --- | --- | --- | --- | --- |
| Mab34 | EPObp | 3.2 × 10$^5$ | 0.017 | 54 |
| EPObp | Fab34 | 4.6 × 10$^5$ | 0.02 | 43 |

Table 1. BIAcore analysis of MAb34 and Fab34 interactions with EPObp. The values for k$_a$ were determined from K$_D$ = k$_d$/k$_a$. Standard errors in all cases were less than 10%.

Example 4

EPO-R Agonist Stimulates Proliferation in Both Recombinant and Non-Recombinant EPO-Dependent Cell Lines Purified MAb34 was tested for its ability to stimulate proliferation of both recombinant and non-recombinant cell lines. Purified MAb34 was able to stimulate proliferation in the EPO-dependent BaF3/EPO-R cell line using the procedure described in Example 2. A dose dependent response evaluation in a [$^3$H]thymidine uptake cell proliferation assay revealed EC$_{50}$ values of approximately 10 nM (FIG. 2A). The effect of MAb34 was specific to EPO-R, because it did not stimulate growth of the parental BaF3 cell line. Based on the maximal amount of [$^3$H]thymidine incorporation, the potency of MAb34 was 8 to 10 -fold lower than the potency of EPO (FIG. 2A). In contrast to the bivalent MAb34, monovalent Fab fragments did not stimulate proliferation of the BaF3/EPO-R cell line (FIG. 2A), although the affinities of MAb34 and Fab34 to EPObp were identical (Table 1).

The cell proliferation experiment was repeated using the EPO-dependent human hematopoietic cell line UT-7/EPO (Komatsu et al. (1993) *Blood* 82, 456–464), which expresses endogenous EPO-R. UT-7/EPO cells (Komatsu et al. (1993) *Blood* 82, 456–464) and were grown in 1× Iscove's Modified Dulbecco's Medium (IMDM) with L-glutamine, 25 mM HEPES, 3.024 g/l sodium bicarbonate, 10% FBS, 1% L-glutamine-penicillin-streptomycin solution (Irvine Scientific) containing 270 pM EPO.

UT-7/EPO cells were grown to approximately 3×10$^5$ cells/ml, collected by centrifugation, washed twice with PBS and resuspended at 50,000 cells/ml in assay medium (RPMI 1640 medium, 1% L-glutamine, 4% FBS). Test samples, 100 μl diluted in assay medium at least 5-fold, were added to wells. Then 50 μl cells were added (5,000 cells per well) and plates were incubated at 37° C. and 5% CO$_2$. After 72 hours, 50 μl methyl-[$^3$H]thymidine (1 mCi/ml; 20 Ci/mmol) diluted 1:100 in assay medium was added. Cells were incubated for another 4 hours at 37° C. and 5% CO$_2$. Labeled cells were harvested onto glass fiber filtermats using a PHD cell harvester (Cambridge Technology, Inc.). Filters were rinsed with 2-propanol, dried and counted in a Beckman Model LS6000IC scintillation counter.

MAb34 was more active in the UT-7/EPO cell line: In UT-7/EPO cells MAb34 stimulated cell proliferation with an $EC_{50}$ of approximately 300 pM (FIG. 2B) as compared to 10 nM for BaF3/EPO-R. The maximum of incorporation was close to the value obtained with EPO. This may be due to the higher concentration of EPO-R molecules on the surface of UT-7/EPO cells, which contain 2400 receptors per cell (Komatsu et al. (1993) *Blood* 82, 456–464; Nicolis et al. (1993) *Exp Hematol* 21, 665–670) compared to 800 for BaF3/EPO-R. The higher the receptor concentration, the lower one should expect the ligand concentration necessary to induce dimerization of the receptors.

Figure 2:
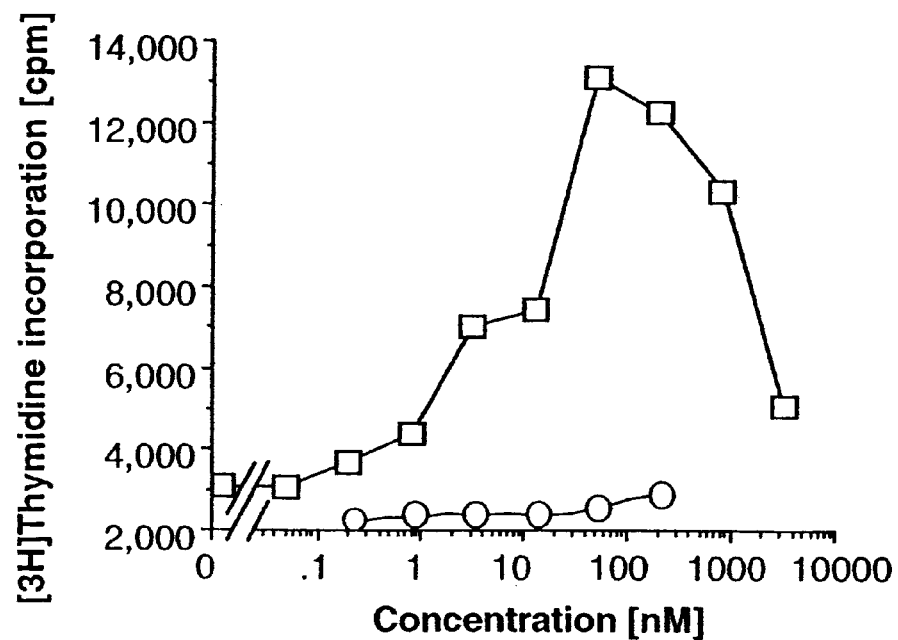
FIG. 2B is a plot of steady state values ($\Delta R_{eq}$) versus EPObp concentrations. The solid line represents a fit of the data to the steady state model described by Karlsson et al. (Karlsson et al. (1991) *J. Immunol Methods* 145, 229–240).
FIG. 2A is a graph showing MAb34-induced proliferation of BaF3/EPO-R cells and Cells were incubated in the presence of [$^3$H]thymidine and various concentrations of MAb34 (open squares) and Fab34 (open circles) as described in Example 4.
Figure 2:
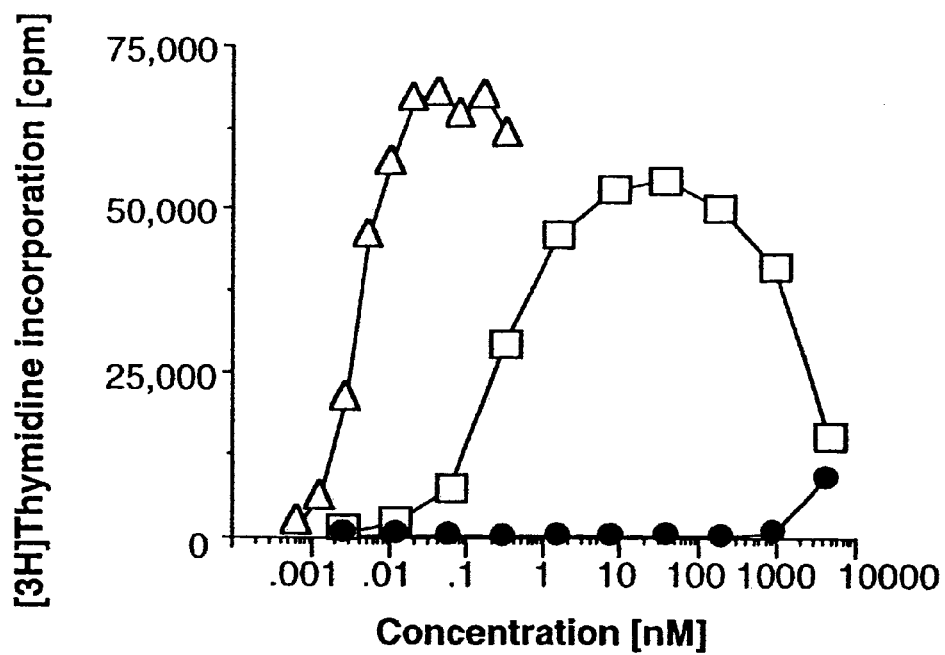

At higher concentrations (above 200 nM) MAb34 antagonizes cell proliferation in both cell lines (FIG. 2). The resulting dose-dependent proliferation curve has a bell-shaped character. MAb34 self-antagonized with $IC_{50}$ values of approximately 2 µM for both cell lines.

If EPO homodimerizes the receptor, then self-antagonism should be observed at high EPO concentrations. We showed this to be the case using an in vitro proliferation assay with BaF3/EPO-R cells. Self-antagonism at high ligand concentrations should also be observed for EPO, if it homodimerizes the receptor. BaF3/EPO-R cells and parental BaF3 cells were assayed over a dose range of 30 pM to 30 µM EPO. Proliferation significantly decreased above 3 µM, but complete inhibition was not observed at the concentrations tested. The estimated $IC_{50}$ value was approximately 20 µM, representing 74,000 U/ml or 370 µg/ml. This is an extremely high concentration: BaF3/EPO-R cells proliferate with an EC50 of 15 pM, which is six orders of magnitude lower. To confirm that the decrease in signal in the BaF3/EPO-R cells was specific to EPO and not due to toxicity or other artifacts at such high ligand concentrations, parental BaF3 cells were incubated with EPO at identical concentrations and in the presence of IL-3 containing WEHI media. No decrease in the IL-3 dependent proliferation was observed.

Example 5

EPO-R Agonist Induces Differentiation of CD34+ Erythroid Progenitor Cells in the Presence of SCF MAb34 was tested for its ability to induce differentiation of erythroid progenitor cells. The differentiation of CD34+ cells to BFUe is dependent on EPO and SCF (Iscove et al. (1974) *J. Cell. Physiol* 83, 309–320). MAb34 was able to induce in vitro differentiation of human CD34+ erythroid cell precursors.

To purify CD34+ erythroid cell precursors, normal human donors were lymphopheresed according to standard protocols. The lymphopheresed cells were washed, resuspended in Hank's Balanced Salt Solution (HBSS) and separated by density centrifugation over a gradient (ficoll-paque). The low-density cells (LD) were collected from the gradient and washed with HBSS and resuspended in PBS supplemented with 0.5% BSA and 5 mM EDTA at a concentration of $5 \times 10^8$ cells/ml. The LD cells were then further purified using a CD34 progenitor Cell Isolation Kit (QBend/10) made by Miltenyi Biotech GmbH. The in vitro BFUe assay was done on purified CD34+ cells in methyl cellulose. The medium contains 20% FBS, 0.33× IMDM (Gibco), salts, 2-mercaptoethanol, nucleosides, cholesterol, sodium pyruvate, Hu-transferrin, lipids, Hu-insulin, deionized BSA and 100 ng/ml Stem Cell Factor (SCF) (Ponting et al. (1994) *Exp. Hematol* 22, 810. To plate out duplicate 1 ml samples, an excess of 3 ml was prepared in sterile polystyrene tubes. Each tube received CD34+ cells (10,000 cells/ml), 0.015 ml SCF (20 µg/ml), and a combination of sample and medium totaling 3 ml. The tubes were mixed and 1 ml was aliquoted onto 35×100 mm tissue culture plates. The plates were incubated at 37° C. and 10% $CO_2$ in a humidified tissue culture incubator. Erythroid colonies (orange to red in color) were scored after 20 days.

In two independent experiments, duplicate sets of CD34+ cells were treated with various concentrations of MAb34, EPO, or a control antibody. After 19 or 20 days, respectively, colonies of BFUe cells were visible in the presence of either MAb34 or EPO, but not in the antibody control (Table 2). The colonies showed typical red color and could be identified as BFUe cells by microscopic analysis. No mixed colonies containing red and white cells were observed. As in the cell proliferation assays described above, EPO was more potent than MAb34. Colonies developed at the lowest EPO concentration tested (1.3 pM), whereas no differentiation was observed below a MAb34 concentration of 7 nM. The absolute number of colonies was higher in the presence of EPO and colonies were larger, containing a higher number of cells. Increasing concentrations of EPO produced larger colonies, whereas the size of colonies formed by MAb34 was not dependent on the concentration of ligand. The approximate $EC_{50}$ value was 15 nM, and the highest stimulation of differentiation by MAb34 observed was between 22 nM and 220 nM, similar to the maxima observed in the cell proliferation assays (Table 2). In addition, at concentrations above 720 nM MAb34 self-antagonizes in this cell differentiation assay. All these data demonstrate that both cell proliferation and differentiation are driven by ligand induced receptor homodimerization.

TABLE 2

BFUe In vitro Differentiation Assay

| Factor | Experiment 1 | | Experiment 2 | |
|---|---|---|---|---|
| | Conc., [nM] | Colonies | Conc., [nM] | Colonies |
| EPO | 0.00254 | 30/22 | 0.0013 | 9/11 |
| | 0.00649 | 31/37 | 0.0026 | 31/27 |
| | 0.0130 | 49/56 | 0.0066 | 46/62 |
| | 0.0259 | 55/61 | 0.0130 | 81/97 |
| | 0.0649 | 73/63 | 0.0259 | 142/100 |
| | | | 0.130 | 133/126 |
| Mab34 | | | 1.8 | 0/0 |
| | 3.6 | 0/0 | 3.6 | 0/0 |
| | 7.2 | 0/2 | 7.2 | 0/0 |
| | 21.6 | 12/10 | 14.4 | 5/6 |
| | 36.0 | 15/3 | 21.6 | 10/7 |
| | 72.0 | 10/7 | 36.0 | 13/12 |
| | 216 | 11/4 | 72.0 | 7/15 |
| | 360 | 4/3 | 144 | 5/14 |
| | 720 | 2/6 | 216 | 4/13 |
| | 1080 | 0/1 | 360 | 6/9 |
| | 1800 | 0/1 | 720 | 0/2 |
| | | | 1080 | 0/0 |
| Mab Control | | | 6.9 | 0/0 |
| | 34.4 | 0/0 | 34.4 | 0/0 |
| | 206 | 0/0 | 206 | 0/0 |
| | 344 | 0/0 | 688 | 0/0 |

Table 2. Purified CD34+ cells (10,000 cells per duplicate sample) were incubated in the presence of the indicated sample as described in the methods section. Erythroid colonies were counted after 19 days (experiment 1) and 20 days (experiment 2), respectively.

Example 6

Agonist Activity of MAB34 Correlates Well with a Model for Antibody-Mediated Receptor Dimerization Mathematical models have been developed described for the formation of receptor dimers on the cell surface by bivalent ligand antibodies (Perelson, A. S. (1984) in *Cell Surface Dynamics: Concepts and Models* (Perelson, A. S., DeLisi, C., and Wiegel, F. W., eds), pp. 223–276, Marcel Dekker, Inc., New York, N.Y.)) or by GH (Ilondo et al. (1994) *Endocrinology* 134, 2937–2403). We investigated how the agonist activity of MAb34 would correlate with the occurrence of receptor dimers predicted by the model of Perelson.

Briefly, Perelson postulates a two step mechanism, where the formation of 1:1 complexes is driven by the affinity constant $K_A$ (=1/$K_D$). Subsequent dimer formation is dependent on a "cross-inking" constant $K_X$, which includes $K_A$ but also depends on the effective concentration of receptors on the cell surface and other factors.

[Ab]+[R]<u>KA</u>[Ab.R]

[Ab.R]+[R]<u>KX</u>[R.Ab.R]

The concentration of dimer is given by:

$$[\text{dimer}] = \frac{[Rtotal]}{2}\left(1 + \frac{1}{2\delta}(1 - \sqrt{1+4\delta})\right)$$

$$\text{where } \delta = \frac{2[AB][Rtotal]KAKX}{(1+2KA[Ab])}$$

assuming that the amount of antibody bound is small compared to the total antibody concentration. The concentration of dimer is solely dependent on $K_A$:

$$[\text{dimer}]\max = \frac{1}{2KA} = \frac{1}{2}KA$$

If the percentage of receptor/antibody 2:1 complexes versus the total number of receptors is plotted against the antibody concentration, a symmetrical bell-shaped curve is predicted. The maximum of 2:1 complexes occurs at a defined antibody concentration equal to one half of the antibody $K_D$ value.

Figure 3:
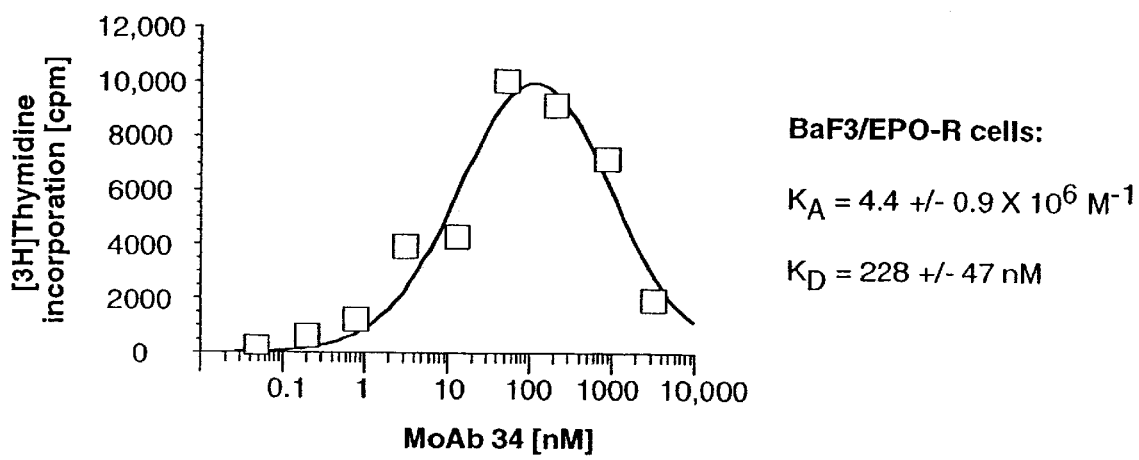
FIG. 3A is a graph showing MAb34-mediated proliferation of BaF3/EPO-R cells.
FIG. 3B is a graph showing Mab34-mediated proliferation of UT-7/EPO cells.
FIG. 3C is a graph showing Mab34-mediated differentiation of CD34$^+$ cells.
Figure 3:
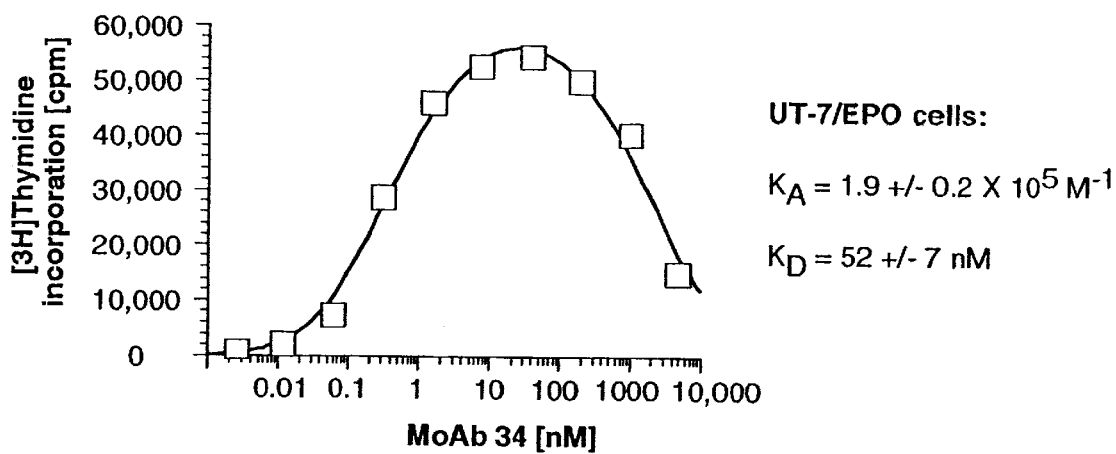
Figure 3:
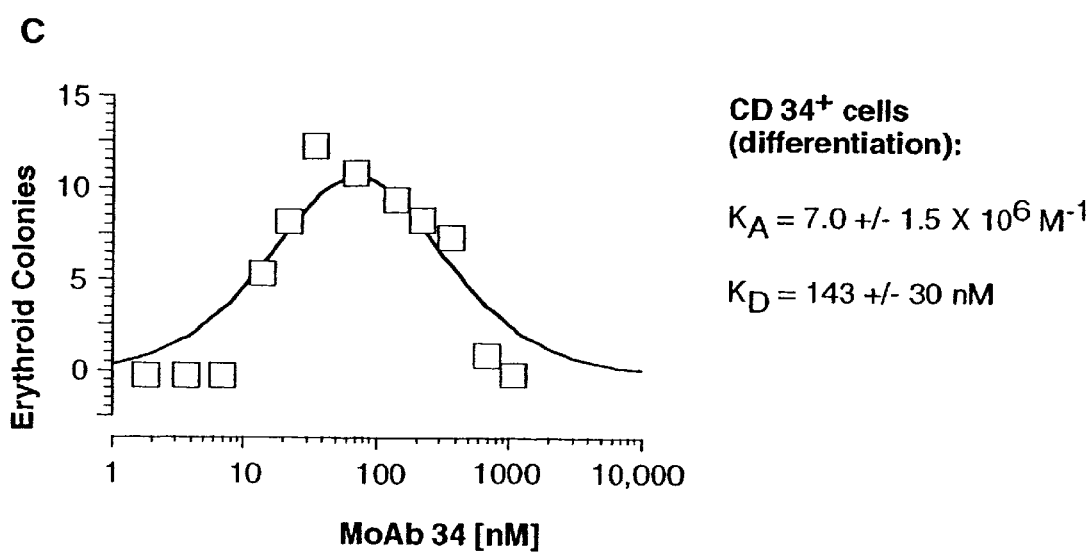

FIG. 3 fits the data of the MAb34 cell proliferation and differentiation assays to the equation. The resulting bell-shaped curves for the proliferation assays correlate well the assay data. The obtained 2:1 complex maxima were 114 nM for BaF3/EPO-R cells and 26 nM for UT-7/EPO cells. According to the model, this translates to apparent KD values of 228 nM and 52 nM respectively, in good agreement with the $K_D$ value of 54 nM determined by BIAcore (Pharmacia) analysis (Table 1). A larger number of parallel experiments would minimize data scattering as is apparent to one of ordinary skill in the art. These results demonstrate that the agonist activity of the bivalent monoclonal antibody MAb34 in cell proliferation and differentiation assays is consistent with ligand induced homodimerization of the EPO-R on the cell surface.

All publications and patent applications mentioned in this specification are herein incorporated by reference to the same extent as if each individual publication or patent application was selectively and individually indicated to be incorporated by reference.

The invention now being fully described, it will be apparent to one of ordinary skill in the art that many changes and modifications can be made thereto without departing from the spirit or scope of the appended claims.

What is claimed is:

1. An antibody produced by Hybridoma #34.10.1 deposited at the ATCC as ATCC HB-12088.

2. A hybridoma cell line Hybridoma #34.10.1 deposited at the ATCC as ATCC HB-12088.

3. A pharmaceutical composition comprising a therapeutically effective amount of the antibody of claim 1.

* * * * *